(12) United States Patent
Richard et al.

(10) Patent No.: US 7,534,421 B2
(45) Date of Patent: May 19, 2009

(54) S-TRIAZINE COMPOUNDS BEARING AT LEAST ONE PARA-AMINOBENZALMALONIC SALT SUBSTITUENT AND PHOTOPROTECTIVE COSMETIC COMPOSITIONS COMPRISED THEREOF

(75) Inventors: Hervé Richard, Villepinte (FR); Bernadette Luppi, Mitry Mory (FR)

(73) Assignee: L'Oreal, Paris (FR)

( * ) Notice: Subject to any disclaimer, the term of this patent is extended or adjusted under 35 U.S.C. 154(b) by 844 days.

(21) Appl. No.: 10/787,940

(22) Filed: Feb. 27, 2004

(65) Prior Publication Data

US 2004/0258636 A1    Dec. 23, 2004

Related U.S. Application Data

(60) Provisional application No. 60/468,995, filed on May 9, 2003.

(30) Foreign Application Priority Data

Mar. 3, 2003    (FR) .................... 03 02562

(51) Int. Cl.
- C07D 251/70 (2006.01)
- C07D 251/50 (2006.01)
- C07D 251/52 (2006.01)
- C07D 403/12 (2006.01)
- C07D 413/12 (2006.01)
- C07D 417/12 (2006.01)
- A61K 31/53 (2006.01)
- A61K 8/49 (2006.01)
- A61Q 17/04 (2006.01)

(52) U.S. Cl. .................... 424/59; 424/60; 524/100; 514/245; 544/197; 544/198; 544/209; 252/401

(58) Field of Classification Search ........... 544/196, 544/209, 197, 198; 514/245; 424/59, 60; 524/100
See application file for complete search history.

(56) References Cited

U.S. PATENT DOCUMENTS

| | | | |
|---|---|---|---|
| 3,242,175 A | 3/1966 | Duennenberger et al. |
| 3,249,608 A | 5/1966 | Hans et al. |
| 3,444,164 A | 5/1969 | Luethi et al. |
| 4,617,390 A | 10/1986 | Hoppe et al. |
| 4,724,137 A | 2/1988 | Hoppe et al. |
| 5,236,698 A | 8/1993 | Richard et al. |
| 5,849,909 A * | 12/1998 | Richard et al. .......... 544/197 |
| 5,955,060 A | 9/1999 | Hueglin et al. |
| 6,017,556 A | 1/2000 | Luther et al. |
| 6,221,342 B1 | 4/2001 | Huglin et al. |
| 6,746,666 B1 | 6/2004 | Luther |
| 2004/0258636 A1 | 12/2004 | Richard et al. |

FOREIGN PATENT DOCUMENTS

| | | |
|---|---|---|
| AT | 287696 T | 2/2005 |
| BE | 639 329 A | 10/1962 |
| BE | 650 932 A | 1/1965 |
| CH | 480 090 A | 10/1969 |
| EP | 0 507 691 A1 | 10/1992 |
| EP | 0 775 698 | 5/1997 |
| EP | 0 790 243 A1 | 8/1997 |
| EP | 0 878 469 A | 11/1998 |
| JP | 58-157774 | 9/1983 |
| JP | 5-230040 | 9/1993 |
| JP | 10-101533 | 4/1998 |
| JP | 9-227533 | 11/1998 |
| JP | 2001-048764 | 2/2001 |
| JP | 2001-515025 | 9/2001 |
| JP | 2003-502354 | 1/2003 |
| WO | WO 95 22959 A | 8/1995 |
| WO | WO 99/08653 | 2/1999 |
| WO | WO 00/78277 A1 | 12/2000 |

OTHER PUBLICATIONS

French Search Report Corresponding to FR 03/02562 Issued on Aug. 29, 2003, 2 Pages.

International Search Report, Dec. 14, 1998 for PCT/EP98/05042.

* cited by examiner

Primary Examiner—Venkataraman Balasubramanian
(74) Attorney, Agent, or Firm—Buchanan, Ingersoll & Rooney P.C.

(57) ABSTRACT

Stable, topically applicable cosmetic/dermatological sunscreen compositions, well suited for the UV-photoprotection of human skin/keratinous materials, contain a thus effective amount of at least one novel s-triazine compound bearing at least one para-aminobenzalmalonic salt substituent.

24 Claims, No Drawings

S-TRIAZINE COMPOUNDS BEARING AT LEAST ONE PARA-AMINOBENZALMALONIC SALT SUBSTITUENT AND PHOTOPROTECTIVE COSMETIC COMPOSITIONS COMPRISED THEREOF

CROSS-REFERENCE TO PRIORITY/PROVISIONAL APPLICATIONS

This application claims priority under 35 U.S.C. § 119 of FR 03/02562, filed Mar. 3, 2003, and of provisional application Ser. No. 60/468,995, filed May 9, 2003, both hereby expressly incorporated by reference and both assigned to the assignee hereof. This application is also a continuation of said '995 provisional.

CROSS-REFERENCE TO COMPANION APPLICATION

Our copending application Ser. No. 10/787,759, filed concurrently herewith and also assigned to the assignee hereof.

BACKGROUND OF THE INVENTION

1. Technical Field of the Invention

The present invention relates to photoprotective compositions comprising s-triazine derivatives containing at least one grafted para-aminobenzalmalonic salt substituent as sunscreens which are active in the UV radiation region.

The present invention also relates to novel s-triazine compounds containing at least one grafted para-aminobenzalmalonic salt substituent and to the various applications thereof.

2. Description of Background and/or Related and/or Prior Art

It is known that radiation with wavelengths between 280 nm and 400 nm allows browning of the human epidermis and that radiation with wavelengths between 280 nm and 320 nm, known as UV-B radiation, gives rise to erythema and skin burns which may be detrimental to the development of a natural tan. For these reasons and also for aesthetic reasons there is increasing demand for means of controlling this natural tanning. It is therefore advisable to screen this UV-B radiation.

It is also known that UV-A rays with wavelengths between 320 nm and 400 nm, which cause browning of the skin, are capable of inducing its impairment, particularly in the case of skin which is sensitive and/or continually exposed to sunlight. UV-A rays give rise in particular to a loss of elasticity in the skin and to the appearance of wrinkles, leading to premature skin aging. They promote the triggering of the erythemal reaction or amplify this reaction in certain individuals, and may even be the origin of phototoxic or photoallergic reactions. Consequently, for aesthetic and cosmetic reasons, such as the preservation of the natural elasticity of the skin, increasing numbers of individuals wish to control the effect of UV-A rays on their skin.

It is therefore desirable to have compounds capable of absorbing both UV-B rays and UV-A rays.

Organic sunscreens are usually formulated in compositions which are in the form of oil-in-water or water-in-oil emulsions. Organic sunscreens, which are generally lipophilic or hydrophilic, are present in solution in one or the other of these phases in amounts appropriate to provide the desired sun protection factor (SPF).

The sun protection factor is the ratio of the irradiation time required for the erythema-forming threshold to be reached in the presence of the sunscreen under test to the irradiation time required for this same threshold to be reached in the absence of the sunscreen.

In addition to their capacity to screen sunlight, the photoprotective compounds must also have good cosmetic properties, effective solubility in customary solvents, and especially in aqueous media, and satisfactory photostability.

SUMMARY OF THE INVENTION

A novel class of water-soluble s-triazine compounds substituted by at least one grafted para-aminobenzalmalonic salt substituent has now been developed, having properties of absorbing UV radiation within the region of UV-B radiation and within the region of shortwave UV-A. These compounds can be incorporated into cosmetic formulations. They exhibit good solubility in aqueous media and good photostability and exhibit satisfactory cosmetic qualities.

The present invention thus features novel water-soluble compounds derived from s-triazine which are substituted by at least one grafted para-aminobenzalmalonic salt substituent, corresponding to formula (1) below, which will later be more fully described.

This invention likewise features cosmetic or dermatological compositions suited for the photoprotection of human skin and keratin materials, comprising, in a cosmetically acceptable medium, at least one compound of formula (1).

Further aspects of the invention will appear from the description which follows.

DETAILED DESCRIPTION OF BEST MODE AND SPECIFIC/PREFERRED EMBODIMENTS OF THE INVENTION

The compounds according to the present invention have the following general formula (1):

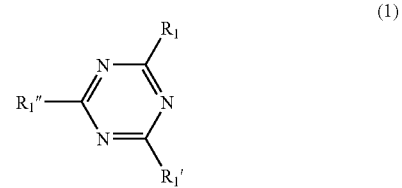

(1)

in which the radicals $R_1$, $R_1'$ and $R_1''$, which may be identical or different, are each:

(i) either a chromophore group of one of the following formulae:

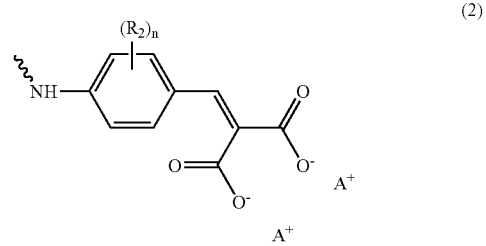

(2)

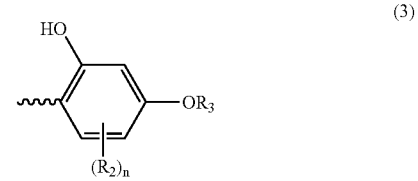

(3)

-continued

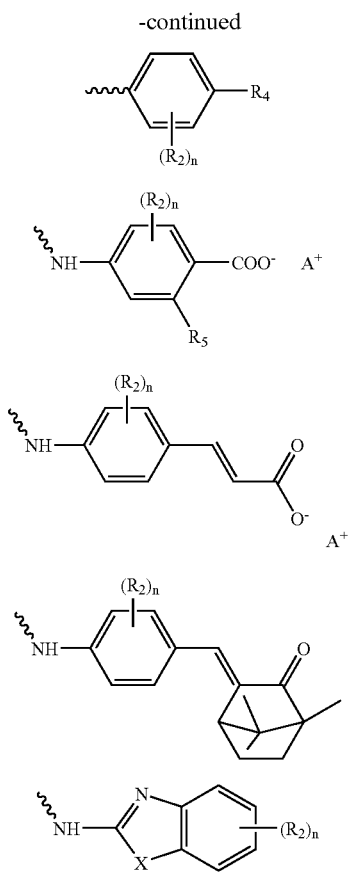

in which $R_2$ is a linear or branched $C_1$-$C_8$ alkyl radical; n is 0, 1 or 2; the radicals A, which may be identical or different, are each hydrogen, an alkali metal cation such as sodium or potassium, an ammonium group, a $C_1$-$C_{20}$ mono-, di- or trialkylammonium radical, a $C_2$-$C_{20}$ mono-, di- or trialkanolammonium radical, or a $C_5$-$C_8$ quaternary nitrogen-containing heterocyclic ring member; $R_3$ is a linear or branched $C_1$-$C_{20}$ alkyl radical, or a linear or branched $C_2$-$C_{20}$ alkenyl radical, said radicals optionally containing one or more oxygen atoms, silicon atoms or trisiloxane groups; $R_4$ is a linear or branched $C_1$-$C_{20}$ alkyl radical, a linear or branched $C_2$-$C_{20}$ alkenyl radical, or a linear or branched $C_1$-$C_{20}$ alkoxy radical, said radicals optionally containing one or more oxygen atoms, silicon atoms or trisiloxane groups; $R_5$ is hydrogen or OH, and X is O, S or $NR_6$, wherein $R_6$ is H or a linear or branched $C_1$-$C_4$ alkyl radical;

with the provisos that at least one of the radicals $R_1$, $R_1{}'$ and $R_1{}''$ is a chromophore group of formula (2) and that not more than one of the radicals $R_1$, $R_1{}'$ and $R_1{}''$ is a chromophore group of formula (3);

(ii) or OH; a linear or branched $C_1$-$C_{20}$ alkoxy radical, or a linear or branched $C_1$-$C_{20}$ mono- or dialkylamino radical, said radicals optionally containing one or more oxygen atoms, silicon atoms or trisiloxane groups.

In the formula (I) above, the alkyl radicals may be selected in particular from methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The particularly preferred alkyl radical is the methyl radical.

In the formulae (I) above, the alkoxy radicals may be selected in particular from methoxy, ethoxy, n-propoxy, isopropoxy, n-butoxy and isobutoxy radicals. The particularly preferred alkoxy radical is the methoxy radical.

In the formula (I) above, the alkenyl radicals may be selected in particular from ethylene, propylene and butene radicals.

In the formula (I) above, the $C_1$-$C_{20}$ mono-, di- or trialkylammonium radicals may be selected in particular from mono-, di- and trimethylammonium and mono-, di- and triethylammonium.

In the formula (I) above, the $C_2$-$C_{20}$ mono-, di- or trialkanolammonium radicals may be selected in particular from mono-, di- and triethanolammonium.

In the formula (I) above, the quaternary heterocyclic ring members may be selected in particular from piperidinium, morpholinium, pyrrolidinium and pyrrolinium.

Among the compounds of formula (I) mention will be made more particularly of those for which:

$R_1$, $R_1{}'$ and $R_1{}''$ are identical or different and are each:

(i) either a chromophore of formula:

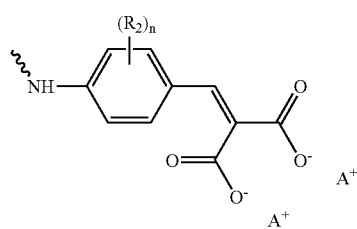

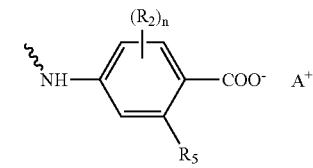

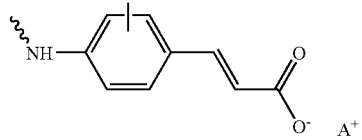

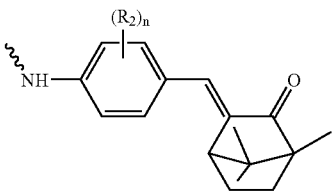

in which A is Na, K or triethanolamine; n=0; and $R_5$ is hydrogen or OH;

(ii) or an OH radical, a $C_1$-$C_4$ alkoxy radical, and more particularly methoxy or butoxy, or a $C_1$-$C_4$ dialkylamino radical, and more particularly dimethylamino.

Among the compounds of formula (I) mention will be made more particularly still of those selected from the following compounds:

(compound a)
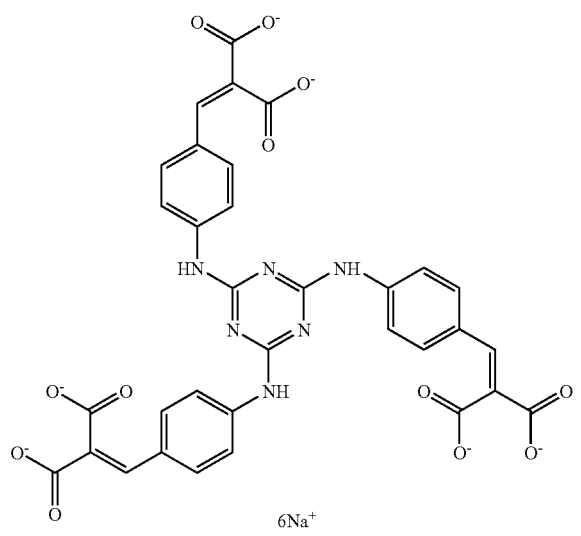
6Na⁺
(compound b)
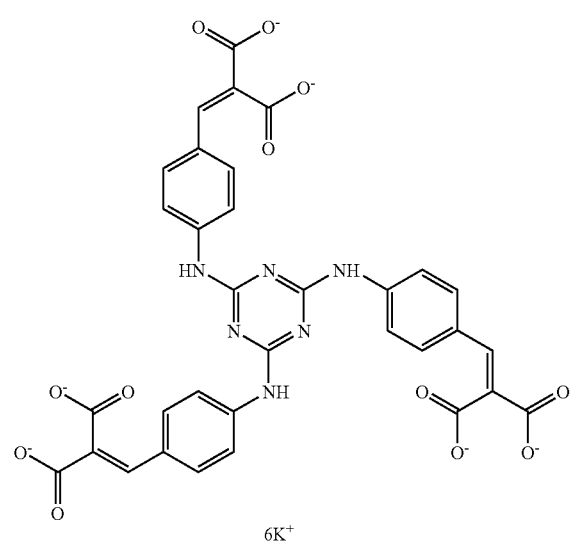
6K⁺
(compound c)
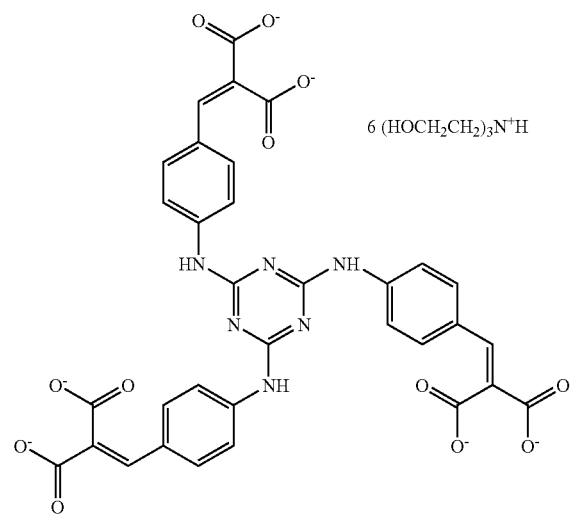
6 (HOCH₂CH₂)₃N⁺H
(compound d)
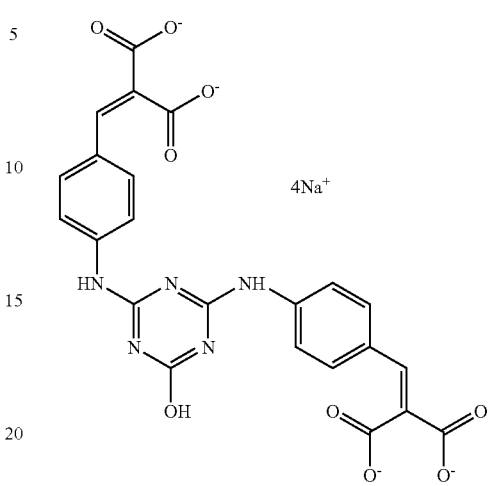
4Na⁺
(compound e)
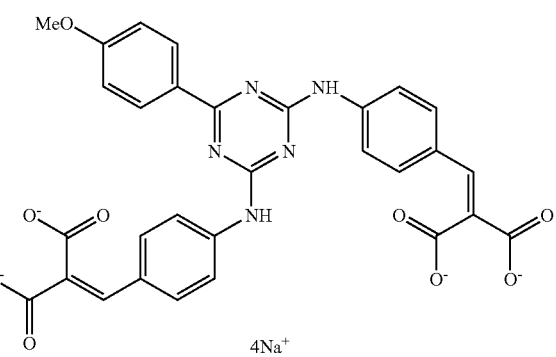
4Na⁺
(compound f)
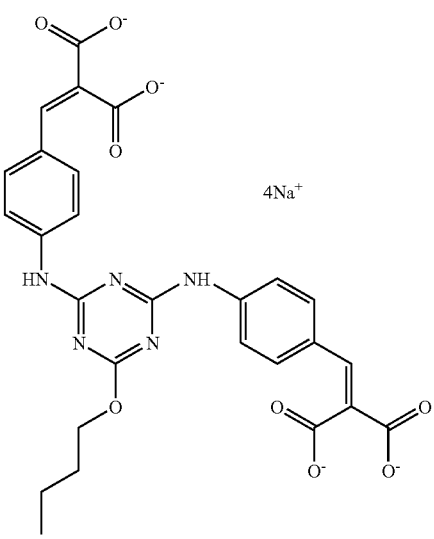
4Na⁺

(compound g)

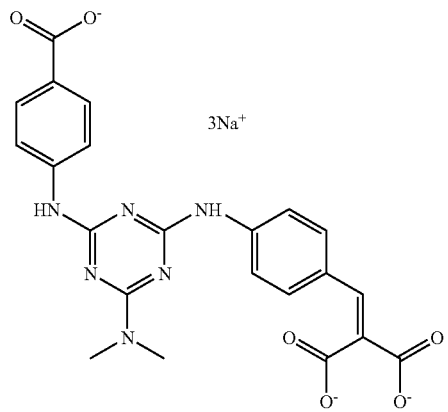

(compound h)

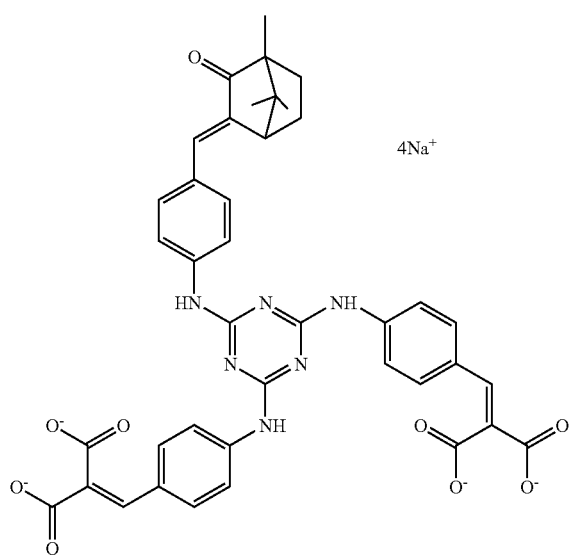

(compound i)

(compound j)

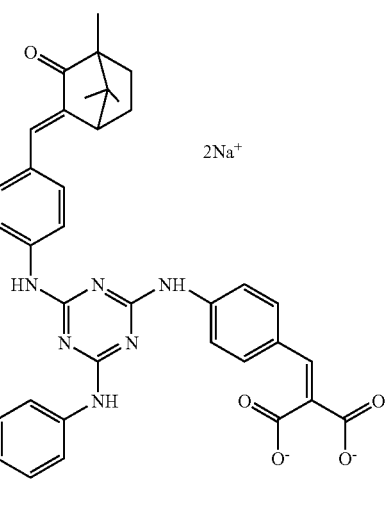

The derivatives of formula (1) are obtainable by the following scheme (pathway A): when one or two of the groups $R_1$, $R_1'$ and $R_1''$ is or are different from the formula (2) these groups are first grafted onto the s-triazine in the same way as in U.S. Pat. No. 4,617,390 (para-aminobenzoate group), EP-507,692 (para-aminobenzylidenecamphor group) or EP-841,341 (various groups) by reacting a 2,4,6-trichloro-s-triazine of formula (A) with a first compound $R_1H$ and then a compound $R_1'H$ by the following scheme (I)

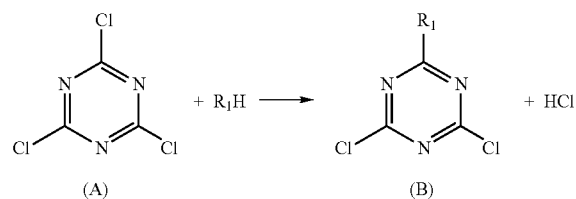

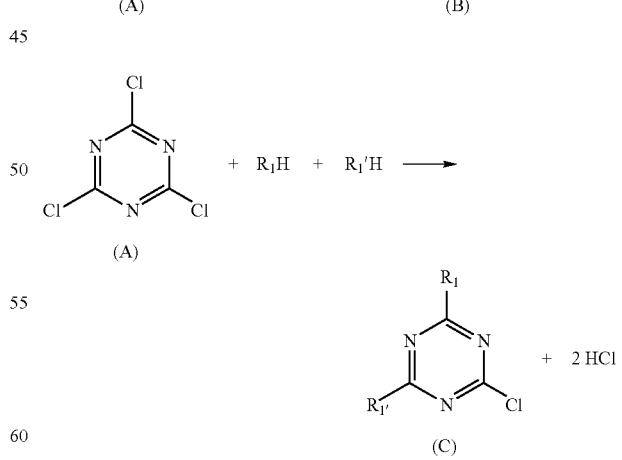

followed by the grafting of one or two groups of formula (2) onto the s-triazine (B) or (C) thus obtained by condensation of an aminobenzalmalonate compound of formula (D) to give the derivative of formula (1) by the following scheme (II):

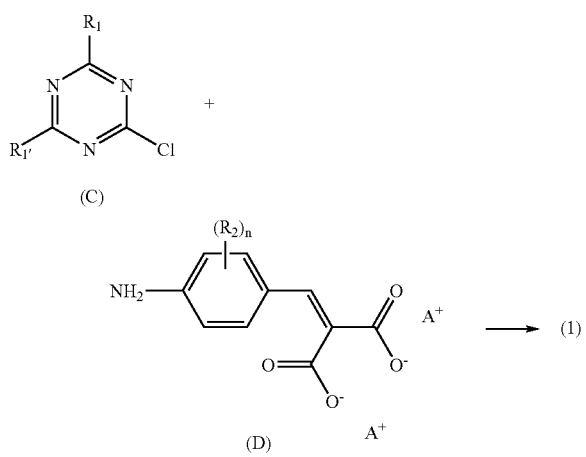

(C)

(D)

if the compound of formula (1) contains one group of formula (2) or else:

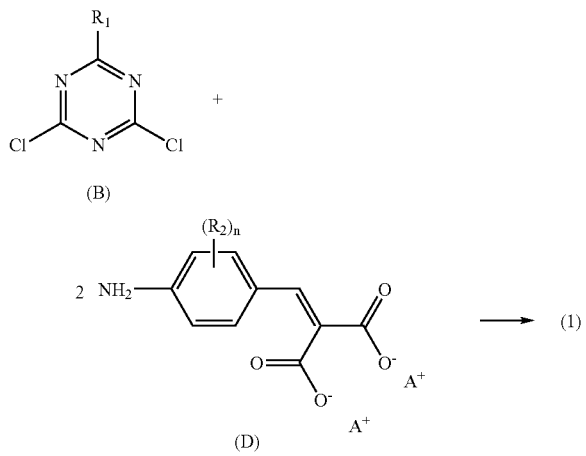

(B)

(D)

if the compound of formula (1) contains two groups of formula (2), the symbols $R_1$, $R_1'$, $R_2$, n and A having the same meanings indicated above for the formula (I).

The compounds of formula (1) containing 3 groups of formula (2) are obtainable by the following scheme (III):

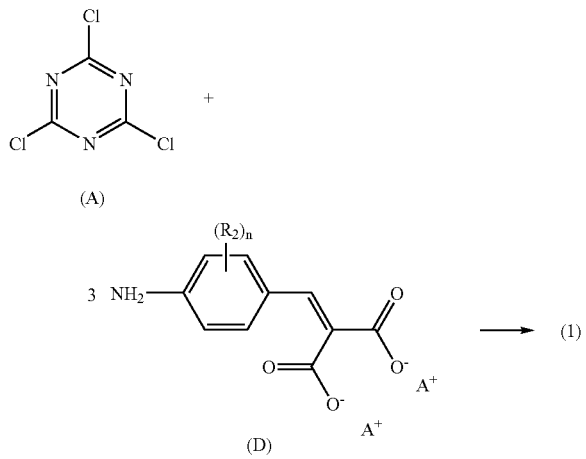

(A)

(D)

The present invention further provides the new synthesis pathway for obtaining salts of benzalmalonate acid derivatives grafted onto s-triazine, which entails reacting a mono-, di- or trichlorinated s-triazine compound of formula (A), (B) or (C), as defined above, with an aminobenzalmalonate compound of formula (D) as defined above.

This synthesis is generally effected in a homogeneous aqueous medium or in suspension and in the presence or absence of an organic cosolvent, the pH being adjusted during the reaction to a level not exceeding 9.5 and more particularly less than 9.0, and at a temperature of between +5° C.-120° C. and more particularly between +5° C.-85° C.

Organic cosolvents which can be used include acetone, THF and toluene.

Basic agents which can be used include sodium hydroxide, potassium hydroxide, sodium carbonate and sodium bicarbonate.

The compounds of formula (1) according to the invention may also be obtained by another synthesis pathway (pathway B), which entails synthesizing the esters corresponding to the compounds of formula (1) and obtaining the compounds of formula (1) by hydrolyzing these esters, in the presence for example of alcoholic sodium hydroxide or potassium hydroxide, to obtain the sodium or potassium salts, respectively, of formulae (1) by the following scheme (IV):

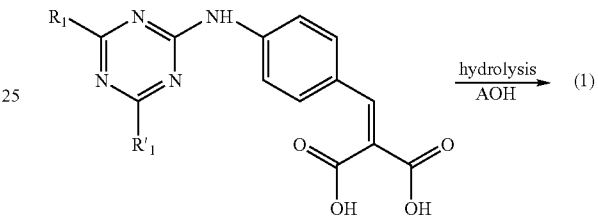

The synthesis of the ester-functional starting products is described for example in EP-0-507,691; to obtain salts other than the sodium or potassium salt it is necessary to proceed via the acid form of the products, by adding concentrated hydrochloric acid to a pH of 2, isolating the acid form and then converting it appropriately to salt form, with an amine for example, to give the corresponding ammonium salt.

The compounds of formula (I) are generally present in the compositions of the invention in proportions of between 0.01% and 20% by weight, preferably between 0.1% and 10% by weight, relative to the total weight of the composition.

The compositions according to the invention may further comprise other, complementary organic or inorganic UV screens which are active in the UVA and/or UVB ranges and which are water-soluble or fat-soluble or else are insoluble in the cosmetic solvents commonly employed.

The complementary organic screens are selected in particular from anthranilates; cinnamic derivatives; dibenzoylmethane derivatives; salicylic derivatives; camphor derivatives; triazine derivatives, such as those described in U.S. Pat. No. 4,367,390, EP-863,145, EP-517,104, EP-570,838, EP-796,851, EP-775,698, EP-878,469, EP-933,376, EP-507, 691, EP-507,692, EP-790,243, EP-944,624; benzophenone derivatives; β,β-diphenylacrylate derivatives; benzotriazole derivatives; benzalmalonate derivatives; benzimidazole derivatives; imidazolines; bis-benzazolyl derivatives as described in EP-669,323 and U.S. Pat. No. 2,463,264; p-aminobenzoic acid (PABA) derivatives; methylenebis(hydroxyphenylbenzotriazole) derivatives, as described in U.S. Pat. Nos. 5,237,071, 5,166,355, GB-2-303,549, DE-1-9,726,184 and EP-893,119; benzoxazole derivatives, as described in EP-0-832,642, EP-1-027,883, EP-1-300,137 and DE-1-0, 162,844; polymer screens and silicone screens, such as those described in particular in WO 93/04665; dimers derived from α-alkylstyrene, such as those described in DE-1-9,855,649; 4,4-diarylbutadienes as described in EP-0-967,200, DE-1-9, 746,654, DE-1-9-755,649, EP-A-1-008,586, EP-1-133,980 and EP-1,133,981, and mixtures thereof.

As examples of complementary organic sunscreens mention may be made of those denoted below by their INCI name:

Para-Aminobenzoic Acid Derivatives:
PABA,
Ethyl PABA,
Ethyl Dihydroxypropyl PABA,
Ethylhexyl Dimethyl PABA, sold in particular under the name Escalol 507 by ISP,
Glyceryl PABA,
PEG-25 PABA, sold under the name Uvinul P25 by BASF.
Salicylic Derivatives:
Homosalate, sold under the name Eusolex HMS by Rona/EM Industries,
Ethylhexyl Salicylate, sold under the name Neo Heliopan OS by Haarmann and Reimer,
Dipropylene glycol salicylate, sold under the name Dipsal by Scher,
TEA Salicylate, sold under the name Neo Heliopan TS by Haarmann and Reimer.
Dibenzoylmethane Derivatives:
Butyl methoxydibenzoylmethane, sold in particular under the trademark Parsol 1789 by Hoffmann La Roche,
Isopropyl Dibenzoylmethane.
Cinnamic Derivatives:
Ethylhexyl methoxycinnamate, sold in particular under the trademark Parsol MCX by Hoffmann La Roche,
Isopropyl Methoxycinnamate,
Isoamyl Methoxycinnamate, sold under the trademark Neo Heliopan E 1000 by Haarmann and Reimer,
Cinoxate, DEA Methoxycinnamate, Diisopropyl Methylcinnamate,
Glyceryl Ethylhexanoate Dimethoxycinnamate.
β,β'-Diphenylacrylate Derivatives:
Octocrylene, sold in particular under the trademark Uvinul N539 by BASF,
Etocrylene, sold in particular under the trademark Uvinul N35 by BASF.
Benzophenone Derivatives:
Benzophenone-1, sold under the trademark Uvinul 400 by BASF,
Benzophenone-2, sold under the trademark Uvinul D50 by BASF,
Benzophenone-3 or oxybenzone, sold under the trademark Uvinul M40 by BASF,
Benzophenone-4, sold under the trademark Uvinul MS40 by BASF,
Benzophenone-5,
Benzophenone-6, sold under the trademark Helisorb 11 by Norquay,
Benzophenone-8, sold under the trademark Spectra-Sorb UV-24 by American Cyanamid,
Benzophenone-9, sold under the trademark Uvinul DS-49 by BASF,
Benzophenone-12
n-hexyl 2-(4-diethylamino-2-hydroxybenzoyl)benzoate.
Benzylidenecamphor Derivatives:
3-Benzylidene camphor, manufactured under the name Mexoryl SD by Chimex,
4-Methylbenzylidene camphor, sold under the name Eusolex 6300 by Merck,
Benzylidene Camphor Sulphonic Acid, manufactured under the name Mexoryl SL by Chimex,
Camphor Benzalkonium Methosulphate, manufactured under the name Mexoryl SO by Chimex,
Terephthalylidene Dicamphor Sulphonic Acid, manufactured under the name Mexoryl SX by Chimex,
Polyacrylamidomethyl Benzylidene Camphor, manufactured under the name Mexoryl SW by Chimex.

Phenylbenzimidazole Derivatives:
Phenylbenzimidazole Sulphonic Acid, sold in particular under the trademark Eusolex 232 by Merck,
Disodium Phenyl Dibenzimidazole Tetra-sulphonate, sold under the trademark Neo Heliopan AP by Haarmann and Reimer.
Triazine Derivatives:
Anisotriazine, sold under the trademark Tinosorb S by Ciba Geigy,
Ethylhexyl triazone, sold in particular under the trademark Uvinul T150 by BASF,
2,4,6-tris(diisobutyl 4'-aminobenzalmalonate)-s-triazine,
Diethylhexyl Butamido Triazone, sold under the trademark Uvasorb Heb by Sigma 3V.
Phenylbenzotriazole Derivatives:
Drometrizole Trisiloxane, sold under the name Silatrizole by Rhodia Chimie, Methylene bis-Benzotriazolyl Tetramethylbutylphenol, sold in solid form under the trademark Mixxim BB/100 by Fairmount Chemical or in micronized form in aqueous dispersion under the trademark Tinosorb M by Ciba Specialty Chemicals.
Anthranilic Derivatives:
Menthyl anthranilate, sold under the trademark Neo Heliopan MA by Haarmann and Reimer.
Imidazoline Derivatives:
Ethylhexyl Dimethoxybenzylidene Dioxoimidazoline Propionate.
Benzalmalonate Derivatives:
Polyorganosiloxanes containing a benzalmalonate function, such as Polysilicone-15, sold under the trademark Parsol SLX by Hoffmann La Roche.
4,4-Diarylbutadiene Derivatives:
1,1-dicarboxy(2,2'-dimethylpropyl)-4,4-diphenylbutadiene.
Benzoxazole Derivatives:
2,4-bis[5-(dimethylpropyl)benzoxazol-2-yl(4-phenyl)imino]-6-(2-ethylhexyl)imino-1,3,5-triazine, sold under the name Uvasorb K2A by Sigma 3V;

and mixtures thereof.

The preferred complementary organic UV screens are selected from:
Ethylhexyl Salicylate,
Ethylhexyl Methoxycinnamate,
Butyl Methoxydibenzoylmethane,
Octocrylene,
Phenylbenzimidazole Sulphonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulphonic Acid,
Disodium Phenyl Dibenzimidazole Tetra-sulphonate,
2,4,6-tris(Diisobutyl 4'-aminobenzalmalonate)-s-triazine,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone-15,
1,1-Dicarboxy(2,2'-dimethylpropyl)-4,4-diphenylbutadiene,
2,4-bis[5-(Dimethylpropyl)benzoxazol-2-yl-(4-phenyl)imino]-6-(2-ethylhexyl)imino-1,3,5-triazine and mixtures thereof.

The complementary inorganic sunscreens are selected from pigments, including nanopigments (mean primary particle size: generally between 5 nm and 100 nm, preferably between 10 nm and 50 nm), of coated or uncoated metal oxides, for example nanopigments of titanium oxide (amorphous or crystalline in rutile and/or anatase form), iron oxide, zinc oxide, zirconium oxide or cerium oxide, which are all well-known UV photoprotectants. Conventional coating agents are, moreover, alumina and/or aluminium stearate. Coated or uncoated metal oxide nanopigments of this kind are described in particular in EP-518,772 and EP-518,773.

The complementary UV screens in accordance with the invention are generally present in the compositions according to the invention in proportions ranging from 0.01% to 20% by weight relative to the total weight of the composition, and preferably ranging from 0.1% to 10% by weight relative to the total weight of the composition.

The cosmetic compositions according to the invention may further comprise tanning and/or artificial skin browning agents (self-tanning agents) such as dihydroxyacetone (DHA).

The compositions in accordance with the present invention may further comprise conventional cosmetic adjuvants, selected in particular from fats, organic solvents, ionic and nonionic thickeners, softeners, humectants, antioxidants, moisturizers, desquamating agents, free-radical scavengers, antipollutants, antibacterials, anti-inflammatories, depigmenting agents, propigmenting agents, opacifiers, stabilizers, emollients, silicones, antifoams, insect repellants, perfumes, preservatives, anionic, cationic, nonionic, zwitterionic and amphoteric surfactants, substance P antagonists, substance CGRP antagonists, fillers, pigments, polymers, propellants, alkalifying or acidifying agents or any other ingredient commonly used in the field of cosmetology and/or dermatology.

The fats may be an oil or wax or mixtures thereof. An oil is a compound which is liquid at ambient temperature. A wax is a compound which is solid or substantially solid at ambient temperature and whose melting point is generally above 35° C.

As oils mention may be made of mineral oils (paraffin); vegetable oils (sweet almond oil, macadamia oil, blackcurrant seed oil, jojoba oil); synthetic oils such as perhydrosqualene; fatty alcohols, acids or esters (such as $C_{12}$-$C_{15}$ alcohol benzoate, sold under the trademark Finsolv TN by Witco, octyl palmitate, isopropyl lanolate, and triglycerides, including those of capric/caprylic acids), ethoxylated or propoxylated fatty ethers and esters; silicone oils (cyclomethicone, polydimethylsiloxanes or PDMS) or fluoro oils, and polyalkylenes.

As waxy compounds mention may be made of paraffin, carnauba wax, beeswax and hydrogenated castor oil.

Among organic solvents mention may be made of lower alcohols and polyols. The latter may be selected from glycols and glycol ethers such as ethylene glycol, propylene glycol, butylene glycol, dipropylene glycol and diethylene glycol.

Thickeners may be selected in particular from crosslinked acrylic polymers such as the Carbomer products, crosslinked acrylate/$C_{10}$-$C_{30}$ alkyl acrylate polymers of the Pemulen type, or the polyacrylate-3 sold under the name Viscophobe DB 1000 by Amerchol; polyacrylamides such as the polyacrylamide $C_{13}$-$C_{14}$ isoparaffin and laureth-7 emulsion which is sold under the name Sepigel 305 by SEPPIC, AMPS homopolymers or copolymers such as Hostacerin AMPS, sold by Clariant, modified or non-modified celluloses and guar gums, such as hydroxypropylguar gum, methylhydroxyethylcellulose and hydroxypropylmethylcellulose, xanthan gum, and nanoscale silicas of Aerosil type.

One skilled in this art will to take care to select the optional complementary compound or compounds mentioned above and/or its or their quantities such that the advantageous properties intrinsically attaching to the compounds in accordance with the invention are not, or not substantially, impaired by the intended addition or additions.

The compositions according to the invention can be prepared by techniques which are well known to this art, especially those intended for the preparation of oil-in-water or water-in-oil emulsions.

This composition may be present in particular in the form of a simple or complex emulsion (O/W, W/O, O/W/O or W/O/W) such as a cream or milk, or in the form of a gel or cream gel, in the form of a lotion, an oil, a powder or a solid stick, and may where appropriate be packaged as an aerosol and be present in the form of a foam or spray.

The compositions according to the invention are preferably in the form of an oil-in-water or water-in-oil emulsion.

When the composition is an emulsion its aqueous phase may comprise a nonionic vesicle dispersion prepared by known methods (Bangham, Standish and Watkins, *J. Mol. Biol.*, 13, 238 (1965), FR-2,315,991 and FR-2,416,008).

When the cosmetic composition according to the invention is used for the care of the human epidermis it may be present in suspension or dispersion form in solvents or fats, in the form of a nonionic vesicle dispersion or else in the form of an emulsion, preferably an oil-in-water emulsion, such as a cream or milk, or in the form of an ointment, gel, cream gel, sun oil, solid stick, powder, aerosol foam or spray.

When the cosmetic composition according to the invention is used for the care of the hair it may be present in the form of a shampoo, lotion, gel, emulsion or nonionic vesicle dispersion and may constitute, for example, a rinsing composition, a composition for application before or after shampooing, before or after coloring or bleaching, before, during or after perming or straightening, a styling or treatment lotion or gel, a lotion or a gel for brushing or setting, a perming or straightening composition or a hair coloring or bleaching composition.

When the composition is used as a makeup product for the nails, lips, eyelashes, eyebrows or skin, such as an epidermal treatment cream, foundation, lipstick, eyeshadow, blusher, mascara or liner, also called eyeliner, it may be present in solid or paste form, anhydrous or aqueous, such as oil-in-water or water-in-oil emulsions, nonionic vesicle dispersions or else suspensions.

By way of indication, for the antisun formulations in accordance with the invention which have a vehicle of the oil-in-water emulsion type, the aqueous phase (containing in particular the hydrophilic screens) represents generally from 50% to 95% by weight, preferably from 70% to 90% by weight, relative to the entirety of the formulation, the oily phase (containing in particular the lipophilic screens) from 5% to 50% by weight, preferably from 10% to 30% by weight, relative to the entirety of the formulation, and the (co)emulsifier(s) from 0.5% to 20% by weight, preferably from 2% to 10% by weight, relative to the entirety of the formulation.

The invention further provides for the use of a compound of formula (I) as defined above in a cosmetic or dermatological composition as a UV radiation screen.

The invention further provides for the use of a compound of formula (I) as defined above in a cosmetic composition as an agent for controlling the change in the color of the skin brought about by UV radiation.

The invention further provides for the use of a compound of formula (I) as defined above as a light stabilizer for synthetic polymers such as plastics or glasses, especially spectacle lenses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of the hexasodium salt of 2-(4-{4,6-bis[4-(2,2-dicarboxyvinyl)phenylamino][1,3,5]triazin-2-ylamino}benzylidene)malonic acid by Pathway A

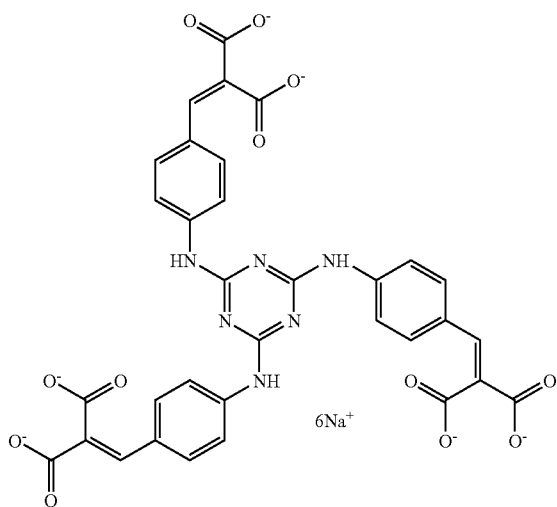

First Step: Preparation of the disodium salt of 2-(4-aminobenzylidene)malonic acid A reactor equipped with a thermometer, a mechanical stirrer and a condenser is charged with piperidine (206.6 g, 2.42 mol). This initial charge is heated to 40° C. Malonic acid is introduced in portions over 15 minutes, without exceeding 70° C. (83.4 g, 0.8 mol). The resulting viscous paste is held at 70° C. and p-aminobenzaldehyde is introduced in portions over 15 minutes (97 g, 0.8 mol). The viscous mixture is left with stirring at 90° C. and the viscosity is monitored. When the viscosity increases, the introduction of isopropyl alcohol is commenced (after 1 hour 15 minutes). 200 ml of isopropyl alcohol are introduced over 2 hours 50 minutes. The mixture is cooled and filtered. The precipitate obtained is washed with a minimal amount of isopropyl alcohol. Drying under vacuum over $P_2O_5$ gives 210 g (yield: 70%) of the dipiperidinium salt of 2-(4-aminobenzylidene)malonic acid in the form of a yellow powder. Subsequently sodium hydroxide (200 ml of 35% strength aqueous sodium hydroxide solution, 1.75 mol) is introduced over 15 minutes at a temperature of 90° C.-70° C., with continued stirring. The mixture is cooled to 40° C. 700 ml of ethanol are added and the reaction mixture is filtered. The solid is taken up in at least 500 ml of water and filtered. This gives approximately 5 g of residue, which is discarded. The filtrate is concentrated to half its volume and 700 ml of 95° ethanol are added, and the product is left to crystallize. Filtration and drying under vacuum over $P_2O_5$ give 140 g (yield: 70%) of the disodium salt of 2-(4-aminobenzylidene)malonic acid in the form of a yellow powder, which is used as it is in the following step.

Second Step: Preparation of 2-(4-[4,6-bis[4-(2,2-dicarboxyvinyl)phenylamino][1,3,5]triazin-2-ylamino}benzylidene)malonic acid In a reactor equipped with a thermometer, a pH measurement system, a mechanical stirrer, a condenser and a dropping funnel, the derivative obtained in the preceding step (108 g, 0.43 mol) is dissolved in 300 ml of water and held at +5° C. At a temperature of less than +5° C., cyanuric chloride (18.4 g, 0.3 equivalent of chlorine) in solution in 350 ml of acetone is added. Following introduction, the pH should be approximately 7. The heterogeneous mixture is heated gradually and acetone is distilled, so as to allow the reaction mixture to be heated to 95° C. The pH is adjusted and kept at 9 using concentrated sodium hydroxide solution. The mixture is heated for 2 hours. After cooling, the liquors are acidified to a pH of 1 using concentrated hydrochloric acid. A fine orange-colored precipitate is formed and is isolated by filtration. The cake obtained is redispersed in water and filtered. Filtration and drying under vacuum over $P_2O_5$ give 56.6 g of orange-colored powder (yield: 81%) of the acid derivative of Example 1:

| UV (ethanol) | $\lambda_{max} = 348$ nm | $\epsilon_{max} = 64\,820$ | $E_{1\%} = 930$ |
|---|---|---|---|

Third Step: Preparation of the Derivative of Example 1

The derivative from the preceding step (5 g, 0.0072 mol) is suspended in 19.9 ml of water. 35% strength aqueous sodium hydroxide solution (4.9 g, 0.043 mol) is added thereto with stirring. This gives the sodium salt derivative of Example 1 in the form of an aqueous solution containing 20% of active substance (sodium salt) with a brown color (pH: 9.8):

| UV (water) | $\lambda_{max} = 323$ nm | $\epsilon_{max} = 86\,428$ | $E_{1\%} = 1\,043$ |
|---|---|---|---|

EXAMPLE 2

Preparation of the hexasodium salt of 2-(4-{4,6-bis[4-(2,2-dicarboxyvinyl)phenylamino][1,3,5]triazin-2-ylamino}benzylidene)malonic acid by Pathway B

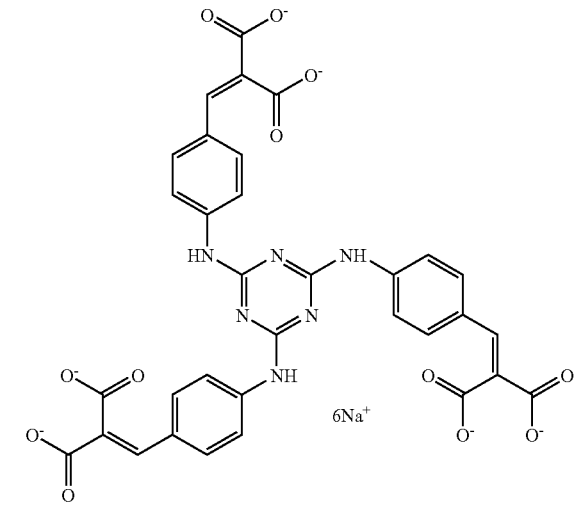

First Step: Preparation of 2-(4-{4,6-bis(4-(2,2-dicarboxyvinyl)phenylamino][1,3,5]triazin-2-ylamino}benzylidene)malonic acid 2,4,6-tris(Diisobutyl 4'-aminobenzalmalonate)-s-triazine (Example of EP-507,691 B1) (10.3 g, 0.01 mol) is dissolved in 150 ml of isopropanol. Excess potassium hydroxide (7.8 g, 0.12 mol) in solution in 50 ml of isopropanol is added. The mixture is refluxed for 2 hours. An insoluble product forms. It is filtered and the precipitate obtained is washed with isopropanol. The solid is dissolved in 50 ml of water. The pH is adjusted to 1 with concentrated hydrochloric acid, with stirring. The solid obtained is isolated by filtration, washed with water and then dried. This gives 5.2 g (yield: 67%) of the acid derivative of Example 2 in the form of a yellow powder.

Second Step: Preparation of the Derivative of Example 2

The derivative from the preceding step (5 g, 0.0072 mol) is suspended in 19.9 ml of water. 35% strength aqueous sodium hydroxide in water (4.9 g, 0.043 mol) is added with stirring. This gives the sodium salt derivative of Example 1 in the form of an aqueous solution containing 20% of active substance (sodium salt), which is pale brown in color (pH 9.6):

| UV (water) | $\lambda_{max}$ = 323 nm | $\epsilon_{max}$ = 87 820 | $E_{1\%}$ = 1 060 |
|---|---|---|---|

EXAMPLE 3

Preparation of the hexapotassium salt of 2-(4-{4,6-bis[4-(2,2-dicarboxyvinyl)phenylamino][1,3,5]triazin-2-ylamino}benzylidene)malonic acid by Pathway B

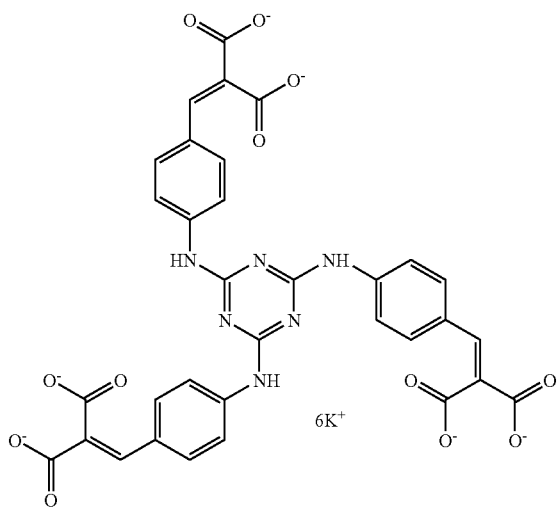

2,4,6-tris(Diisobutyl 4'-aminobenzalmalonate)-s-triazine (Example 1 of Patent EP 507 691 B1) (10.3 g, 0.01 mol) is dissolved in 150 ml isopropanol. Excess potassium hydroxide (7.8 g, 0.12 mol) in solution in 50 ml isopropanol is added. The mixture is refluxed for 2 hours. An insoluble product is formed. It is isolated by filtration and the precipitate obtained is washed copiously with isopropanol. Drying under vacuum over $P_2O_5$ gives 9.2 g (yield: 100%) of the derivative of Example 3 in the form of a brick-red solid which turns yellow in air:

| UV (water) | $\lambda_{max}$ = 324 nm | $\epsilon_{max}$ = 66 600 | $E_{1\%}$ = 720 |
|---|---|---|---|

EXAMPLE 4

Preparation of the hexatriethanolamine salt of 2-(4-{4,6-bis[4-(2,2-dicarboxyvinyl)phenylamino][1,3,5]triazin-2-ylamino}benzylidene)malonic acid by Pathway A

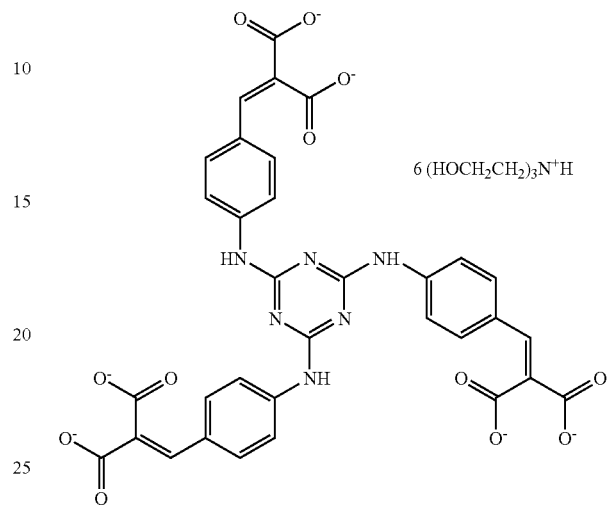

The derivative from the second step of Example 1 (5 g, 0.0072 mol) is suspended in 26.6 ml of water. Triethanolamine (6.4 g, 0.043 mol) is added with stirring. This gives the triethanolamine salt derivative of Example 4 in the form of an aqueous solution containing 30% of active substance (triethanolamine salt) which is pale brown in color (pH 7.3):

| UV (water) | $\lambda_{max}$ = 322 nm | $\epsilon_{max}$ = 83 250 | $E_{1\%}$ = 523 |
|---|---|---|---|

EXAMPLE 5

Preparation of the tetrasodium salt of 2-(4-{4-[4-(2,2-dicarboxyvinyl)phenylamino]-6-hydroxy[1,3,5]triazin-2-ylamino}benzylidene)malonic acid by Pathway A

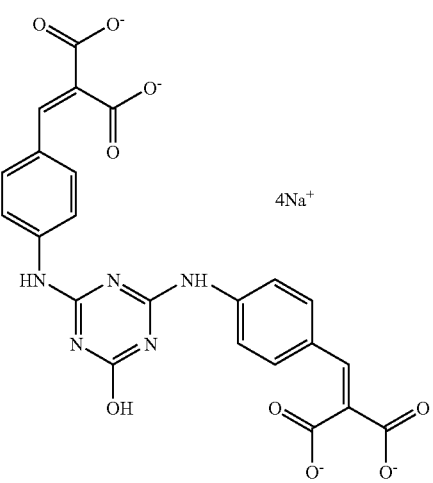

19

First Step: Preparation of the dipotassium salt of 2-(4-aminobenzylidene)malonic acid The dipiperidinium salt of 2-(4-aminobenzylidene)malonic acid obtained in the first step of Example 1 (210 g) is added to 85% potassium hydroxide (114 g, 1.75 mol) in solution in 200 ml of 96% ethanol over 15 minutes at a temperature of 90° C.-70° C., with continual stirring.

The mixture is cooled to 40° C. 700 ml of 96% ethanol are added and the reaction mixture is filtered. The solid is taken up in at least 500 ml of water and filtered. The filtrate is concentrated to half its volume, 500 ml of isopropanol are added, and the product is allowed to crystallize.

Filtration and drying under vacuum over $P_2O_5$ give 205 g (yield: 90%) of the dipotassium salt of 2-(4-aminobenzylidene)malonic acid in the form of a light-yellow powder, which is used as it is in the following step.

Second Step: Preparation of 2-(4-{4-chloro-6-[4-(2, 2-dicarboxyvinyl)phenylamino][1,3,5]triazin-2-ylamino}benzylidene)malonic acid In a reactor equipped with a thermometer, a pH measurement system, a mechanical stirrer, a condenser and a dropping funnel, the derivative obtained in the preceding step (124.6 g, 0.44 mol) is dissolved in 800 ml of water and is kept at +5° C. At a temperature of less than +5° C., cyanuric chloride (36.9 g, 0.2 chlorine equivalent) in solution in 700 ml of acetone is added. After it has been introduced, the pH should be approximately 7. The heterogeneous mixture is heated gradually and the acetone is distilled so as to allow the reaction mixture to be heated to 95° C. The pH is adjusted to and maintained at 9 with potassium hydroxide. The mixture is heated for 2 hours. After cooling, the liquors are acidified to a pH of 1 with concentrated hydrochloric acid. A fine orange-yellow precipitate is formed. It is isolated by filtration. The cake obtained is redispersed in water and filtered. Filtration and drying under vacuum over $P_2O_5$ give 91.3 g (yield: 90%) of 2-(4-{4-chloro-6-[4-(2,2-dicarboxy-vinyl)phenylamino][1, 3,5]triazin-2-ylamino}benzylidene)malonic acid in the form of an orange-red powder:

| UV (NaOH 0.1 N) | $\lambda_{max} = 320$ nm | $\epsilon_{max} = 64\,960$ | $E_{1\%} = 932$ |

Third Step: Preparation of 2-(4-{4-[4-(2,2-dicarboxy-vinyl)phenylamino]-6-hydroxy[1,3,5]triazin-2-ylamino}benzylidene)malonic acid The derivative from the preceding step (50 g, 0.095 mol) is suspended in 500 ml of water. 35% strength aqueous sodium hydroxide is added with stirring until a pH of 12 is obtained. The mixture is heated at 95° C. with stirring for 2 hours and then cooled. The medium is acidified to a pH of 1 using concentrated hydrochloric acid. Filtration, copious washings with water and drying under vacuum over $P_2O_5$ give 52.4 g (yield: 100%) of 2-(4-{4-[4-(2,2-dicarboxyvinyl)phenylamino]-6-hydroxy[1,3,5]triazin-2-ylamino}benzylidene) malonic acid in the form of an orange-red powder

| UV (DMSO/ethanol) | $\lambda_{max} = 336$ nm | $\epsilon_{max} = 35\,070$ | $E_{1\%} = 691$ |

20

Fourth Step: Preparation of the Derivative of Example 5

The derivative obtained in the preceding step (10 g, 0.02 mol) is suspended in 43.8 ml of water. 35% strength sodium hydroxide (3.16 g, 0.079 mol) is added with stirring. This gives the sodium salt derivative of Example 5 in the form of an aqueous solution containing 20% active substance (sodium salt) which is pale brown in color (pH 9.2):

| UV (NaOH, 0.1 N) | $\lambda_{max} = 322$ nm | $\epsilon_{max} = 50\,700$ | $E_{1\%} = 852$ |

EXAMPLE 6

Preparation of the tetrasodium salt of 2-{4-[4-[4-(2, 2-dicarboxyvinyl)phenylamino]-6-(4-methoxyphenyl)[1,3,5]triazin-2-ylamino]benzylidene}malonic acid by Pathway A

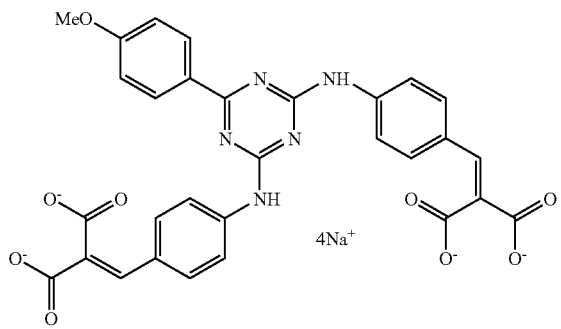

First Step: Preparation of 2,4-dichloro-6-(4-methoxy-phenyl)[1,3,5]triazine

A 1-litre reactor is charged under nitrogen with cyanuric chloride (36.9 g, 0.2 mol) and then with 50 ml of THF. The suspension is cooled to 5-10° C. With stirring, at a temperature of less than 10° C., a 0.5M solution of para-methoxyphenylmagnesium in THF (400 ml, 0.2 mol) is run in under inert gas over 45 minutes. The reaction mixture is left to stand overnight. The solvent is evaporated on a rotary evaporator. The residue is poured into acidified water. Following extraction with dichloromethane, the organic phase is washed with water and dried over sodium sulphate. The solvent is evaporated. The crude solid obtained is triturated with isopropanol and then filtered. The solid is dissolved in hot toluene. Addition of the same volume of heptane precipitates the product. The precipitate is cooled, isolated by filtration and dried. This gives 31.7 g (yield: 62%) of 2,4-dichloro-6-(4-methoxyphenyl)[1,3,5]triazine in the form of a beige powder (m.p. 133-136° C.), which is used as it is in the following step.

Second Step: Preparation of 2-{4-[4-[4-(2,2-dicarboxy-vinyl)phenylamino]-6-(4-methoxyphenyl)[1,3, 5]triazin-2-ylamino]benzylidene}malonic acid The disodium salt of 2-(4-aminobenzylidene)malonic acid (obtained in the first step of Example 1) (10.4 g, 0.04 mol) is dissolved in 50 ml of water. The derivative from the preceding step (5.1 g, 0.02 mol) in solution in 100 ml of acetone is added at 40° C. The pH is held at 12 by introducing concentrated sodium hydroxide solution. Acetone is distilled until the temperature is 75° C. The medium becomes virtually homogeneous. After an hour the reaction is stopped and the medium is cooled. The pH is adjusted to 1 with concentrated hydrochloric acid, with stirring. The solid obtained is isolated by filtration, washed with water and then dried. This gives 9.7 g (yield: 81%) of the acid derivative of Example 6 in the form of an orange-red solid:

| UV (ethanol) | $\lambda_{max}$ = 337 nm | $\epsilon_{max}$ = 47 200 | $E_{1\%}$ = 790 |
| | $\lambda_{max}$ = 306 nm (shoulder) | $\epsilon_{max}$ = 37 900 | $E_{1\%}$ = 634 |

Third Step: Preparation of the Derivative of Example 6

The derivative from the preceding step (5 g, 0.0084 mol) is suspended in 22 ml of water. 35% strength aqueous sodium hydroxide solution (1.35 g, 0.0334 mol) is added with stirring. This gives the sodium salt derivative of Example 6 in the form of an aqueous solution containing 20% of active substance which is brown in color (pH 9.5):

| UV (water) | $\lambda_{max}$ = 318 nm | $\epsilon_{max}$ = 45 900 | $E_{1\%}$ = 768 |

EXAMPLE 7

Preparation of the tetrasodium salt of 2-(4-{4-butoxy-6-[4-(2,2-dicarboxyvinyl)phenylamino][1,3,5]triazin-2-ylamino}benzylidene)malonic acid via Pathway A

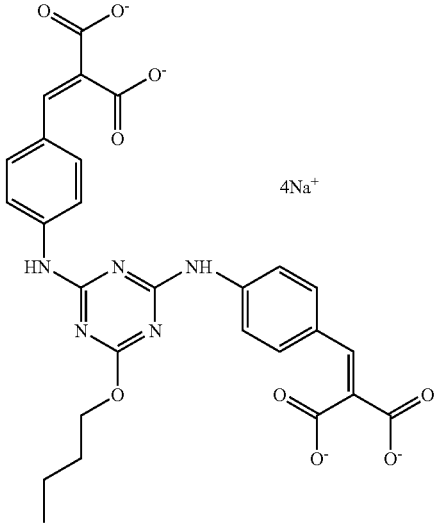

First Step: Preparation of 2-(4-{4-butoxy-6-[4-(2,2-dicarboxyvinyl)phenylamino][1,3,5]triazin-2-ylamino}benzylidene)malonic acid The disodium salt of 2-(4-aminobenzylidene)malonic acid (obtained in the first step of Example 1) (11.31 g, 0.045 mol) is dissolved in 50 ml of water. 2-n-Butoxy-4,6-dichloro-1,3,5-triazine (5 g, 0.0225 mol) in solution in 60 ml of acetone is added at 50° C. over 30 minutes. The pH is held at 9 by introduction of sodium hydroxide solution. Acetone is distilled off until the temperature is 75° C. The medium remains homogeneous. After 2 hours the reaction is stopped and the medium is cooled. The pH is adjusted to 1 with hydrochloric acid, with stirring. The solid obtained is isolated by filtration, washed with water and then dried. This gives 7.15 g (yield: 56%) of the acid derivative of Example 7 in the form of a very fine orange-red powder.

Second Step: Preparation of the Derivative of Example 7

The derivative from the preceding step (5 g, 0.0089 mol) is suspended in 22.5 ml of water. 35% strength aqueous sodium hydroxide solution (1.42 g, 0.0335 mol) is added with stirring. This gives the sodium salt derivative of Example 7 in the form of an aqueous solution containing 20% active substance which is brown in color (pH: 9.2):

| UV (water) | $\lambda_{max}$ = 317 nm | $\epsilon_{max}$ = 51 960 | $E_{1\%}$ = 922 |

EXAMPLE 8

Preparation of the trisodium salt of 2-{4-[4-carboxyphenylamino)-6-dimethylamino[1,3,5]triazin-2-ylamino]benzylidene}malonic acid by Pathway A

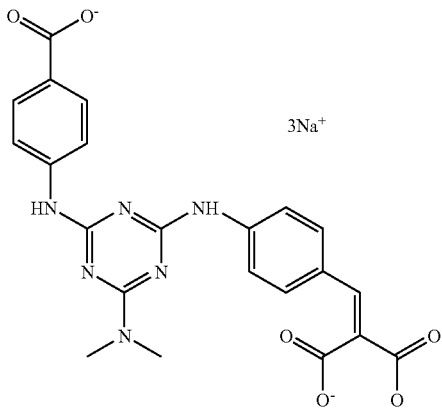

First Step: Preparation of 2-(butyl 4'-minobenzoate)-4,6-dichloro-s-triazine

A solution of cyanuric chloride (18.4 g, 0.1 mol) in 100 ml of acetone/50 ml of water is admixed dropwise at 0-5° C. with butyl 4-aminobenzoate (19.32 g, 0.1 mol) in solution in 200 ml of acetone and then with 100 ml of 0.1N sodium bicarbonate over 1 hour. Stirring is maintained for 1 hour. Isolation of the precipitate by filtration with suction, washing with water and drying give 2-(butyl 4'-minobenzoate)-4,6-dichloro-s-triazine (33 g, yield: 96%) in the form of a white powder (m.p.: 248° C.) which is used as it is in the following step.

Second Step: Preparation of 2-{4-[4-carboxyphenylamino)-6-dimethylamino[1,3,5]triazin-2-ylamino]benzylidene}malonic acid The disodium salt of 2-(4-aminobenzylidene)malonic acid (obtained in the first step of Example 1 (2.94 g, 0.012 mol, 100% excess) is dissolved in 20 ml of water. The preceding derivative (2 g, 0.0058 mol) in solution in 30 ml of acetone is added at 50° C. over 30 minutes in the presence of 5 ml of DMF in order to homogenize the medium (the purpose of this DMF was to release N,N-dimethylamine). The pH is maintained at 12 by introduction of concentrated sodium hydroxide solution. The acetone is distilled off until the temperature is 70° C. The medium remains homogeneous. After 2 hours the reaction is stopped and the medium cooled. The pH is adjusted to 1 using concentrated hydrochloric acid, with stirring. The solid obtained is isolated by filtration, washed with water and then dried. This gives 2.34 g (yield: 85%) of the acid derivative of Example 8 in the form of a yellow powder:

| UV (DMF) | $\lambda_{max}$ = 338 nm | $\epsilon_{max}$ = 34 440 | $E_{1\%}$ = 740 |
|---|---|---|---|
| UV (DMF) | $\lambda_{max}$ = 303 nm | $\epsilon_{max}$ = 40 370 | $E_{1\%}$ = 870 |

Third Step: Preparation of the Derivative of Example 8

The derivative from the preceding step (1 g, 0.0022 mol) is suspended in 4.57 ml of water. 35% strength aqueous sodium hydroxide solution (0.264 g, 0.0066 mol) is added with stirring. This gives the sodium salt derivative of Example 8 in the form of an aqueous solution containing 20% active substance which is yellow in color (pH 9.5):

| UV (water) | $\lambda_{max}$ = 317 nm (shoulder) | $\epsilon_{max}$ = 43 750 | $E_{1\%}$ = 943 |
|---|---|---|---|
| | $\lambda_{max}$ = 302 nm | $\epsilon_{max}$ = 46 630 | $E_{1\%}$ = 1 005 |

EXAMPLE 9

Preparation of the pentasodium salt of 2-(4-{4-[4-(2-carboxyvinyl)phenylamino]-6-[4-(2,2-dicarboxy-vinyl)phenylamino][1,3,5]triazin-2-ylamino}benzylidene)malonic acid by Pathway B

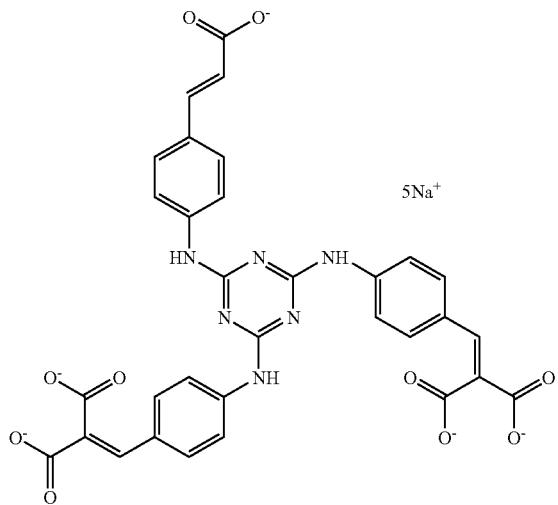

First Step: Preparation of 2-{4-[4-carboxyphenylamino)-6-dimethylamino[1,3,5]triazin-2-ylamino]benzylidene}malonic acid by Pathway B 2,4-bis(Diisobutyl 4'-aminobenzalmalonate)-6-(2-ethylhexylamino)-s-triazine (obtained in Example 6 of Patent EP 0 507 691) (3 g, 0.003 mol) is dissolved in 40 ml of isopropanol. Potassium hydroxide (2.6 g, 0.058 mol) in solution in 20 ml of isopropanol is added. The mixture is refluxed. An insoluble product is formed. Water is added gradually and heating is continued for 2 hours. The isopropanol is evaporated off. The pH is adjusted to 1 using concentrated hydrochloric acid, with stirring. The solid obtained is isolated by filtration, washed with water and then dried. This gives 1.32 g (yield: 67%) of the acid derivative of Example 9 in the form of a yellow powder.

Second Step: Preparation of the Derivative of Example 9

The derivative from the preceding step (1 g, 0.00153 mol) is suspended in 4.53 ml of water. 35% strength aqueous sodium hydroxide solution (0.31 g, 0.077 mol) is added with stirring. This gives the sodium salt derivative of Example 9 in the form of an aqueous solution containing 20% active substance which is yellow in color (pH: 9.5):

| UV (water) | $\lambda_{max}$ = 327 nm | $\epsilon_{max}$ = 83 070 | $E_{1\%}$ = 1 274 |
|---|---|---|---|

EXAMPLE 10

Preparation of the tetrasodium salt of 2-(4-{4-[4-(2-dicarboxyvinyl)phenylamino]-6-[4-(4,7,7-trimethyl-3-oxobicyclo[2.2.1]hept-2-ylidenemethyl)phenylamino][1,3,5]triazin-2-ylamino}benzylidene)malonic acid by Pathway B

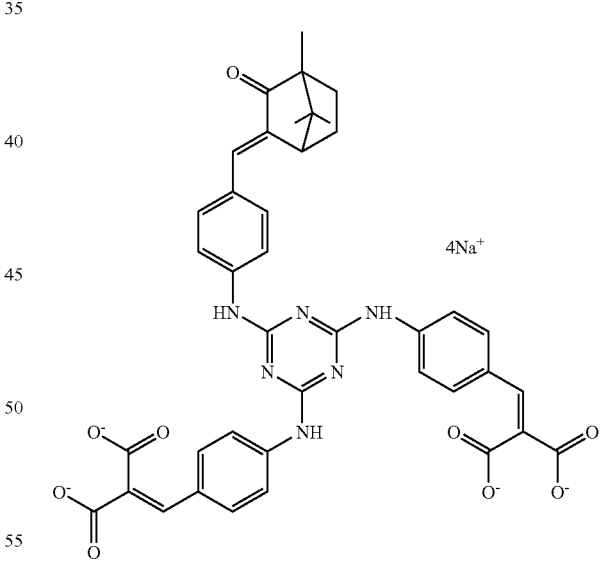

First Step: Preparation of 2-(4-{4-[4-(2-dicarboxy-vinyl)phenylamino]-6-[4-(4,7,7-trimethyl-3-oxobicy-clo[2.2.1]hept-2-ylidenemethyl)phenylamino][1,3,5]triazin-2-ylamino}benzylidene)malonic acid 2,4-bis(Diisobutyl 4'-aminobenzalmalonate)-6-(4'-aminobenzylidenecamphor)-s-triazine (obtained in Example 9 of Patent EP 0 507 691) (7 g, 0.0072 mol) is dissolved in 100 ml of isopropanol. Potassium hydroxide (3.24 g, 0.058 mol) in solution in 20 ml of isopropanol is added. The mixture is refluxed for 1 hour. The insoluble product formed is isolated by filtration and washed copiously with isopropanol. The brick-red solid obtained turns yellow in air. The solid is taken up in water and acidified to a pH of 1 with hydrochloric acid. The solid obtained is isolated by filtration, washed with water and then dried. This gives 4.6 g (yield: 86%) of the acid derivative of Example 10 in the form of an orange-yellow powder.

Second Step: Preparation of the Derivative of Example 10

The derivative from the preceding step (2 g, 0.00268 mol) is suspended in 8.73 ml of water. 35% strength aqueous sodium hydroxide solution (0.43 g, 0.0107 mol) is added with stirring. This gives the sodium salt derivative of Example 10 in the form of an aqueous solution containing 20% of active substance which is pale yellow in color (pH: 9.0):

| UV (water) | $\lambda_{max}$ = 329 nm | $\epsilon_{max}$ = 69 210 | $E_{1\%}$ = 963 |

EXAMPLE 11

Preparation of the disodium salt of 2-(4-{[4,6-bis({4-(4,7,7-trimethyl-3-oxobicyclo[2.2.1]hept-2-ylidene)methyl]phenyl}amino)[1,3,5]triazin-2-ylamino}benzylidene)malonic acid by Pathway B

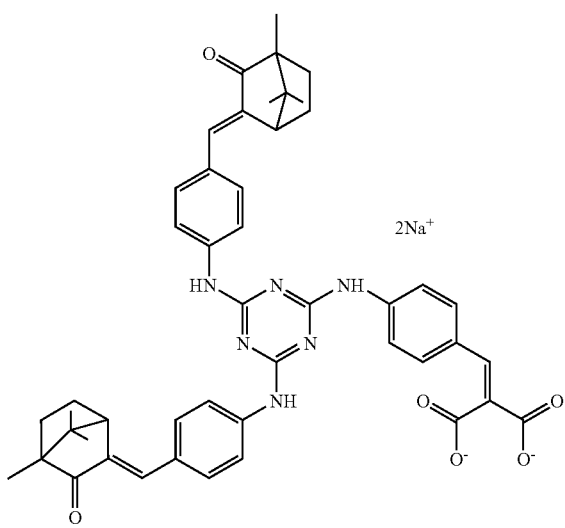

First Step: Preparation of 2-(4-{[4,6-bis({4-(4,7,7-trimethyl-3-oxobicyclo[2.2.1]hept-2-ylidene)methyl]phenyl}amino)[1,3,5]triazin-2-ylamino}benzylidene) malonic acid 2,4-Bis(diisobutyl 4'-aminobenzylidenecamphor)-6-(4'-aminobenzalmalonate)-s-triazine (obtained in Example 2 of Patent EP 0 507 692) (1.5 g, 0.0017 mol) is dissolved in a mixture of ethanol and aqueous sodium hydroxide. The mixture is refluxed for 7 hours. The insoluble product formed is isolated by filtration and washed copiously with isopropanol.

After cooling, a precipitate is formed. It is isolated by filtration. The filtration liquors are acidified to a pH of 1 with hydrochloric acid. The solid obtained is isolated by filtration, washed with water and then dried. This gives 0.33 g (yield: 24%) of the acid derivative of Example 11 in the form of a yellow powder.

Second Step: Preparation of the Derivative of Example 11

The derivative from the preceding step (0.33 g, 4.2×10$^{-4}$ mol) is suspended in 7.03 ml of water. 35% strength aqueous sodium hydroxide solution (0.033 g, 4.2×10$^{-4}$ mol) is added with stirring. This gives the sodium salt derivative of Example 11 in the form of an aqueous solution containing 5% active substance which is pale yellow in color (pH: 8.5):

| UV (water) | $\lambda_{max}$ = 353 nm | $\epsilon_{max}$ = 98 170 | $E_{1\%}$ = 1 238 |

EXAMPLE 12

Antisun Composition (Oil-in-Water Emulsion)

| | |
|---|---|
| Compound of Example 4 (aqueous solution of triethanolamine salt containing 30% AS) | 6 g |
| 80/20 mixture of cetylstearyl alcohol and ethoxylated cetylstearyl alcohol (33 EO units) sold by Tensia under the trademark Dehsconet ® 390 | 7 g |
| Mixture of glycerol monostearate and distearate, sold under the trademark Cerasynth ® SD by ISP | 2 g |
| Cetyl alcohol | 1.5 g |
| Polydimethylsiloxane sold under the name DC200Fluid ® by Dow Corning | 1.5 g |
| Glycerol | 15 g |
| Preservatives | Qs |
| Demineralized water    qs | 100 g |

The fatty phase is heated at approximately 70-80° C. until melting is complete. The aqueous phase, containing the compound of Example 4, is subsequently added in one go at 80° C. with vigorous stirring. Stirring is maintained for 10 to 15 minutes and then the mixture is allowed to cool with moderate stirring, to approximately 40° C., and the preservatives are added. This pale yellow antisun cream which is particularly effective against UV-B.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A water-soluble substituted s-triazine compound having the formula (1):

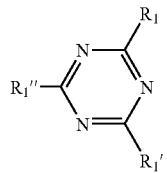
(1)

in which two of the radicals $R_1$, $R_1'$ and $R_1''$ are of the formulae:

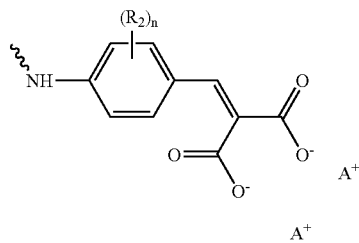
(2)

and the other radical, which may be identical or different, is either:

(i) a chromophore group of one of the following formulae:

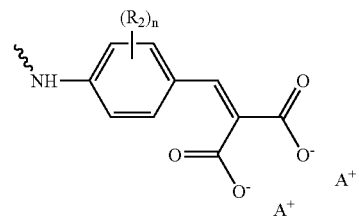
(2)

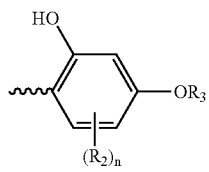
(3)

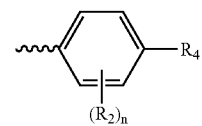
(4)

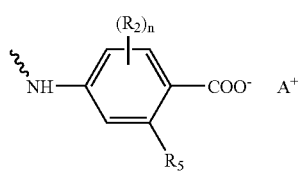
(5)

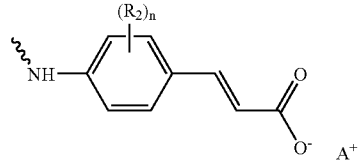
(6)

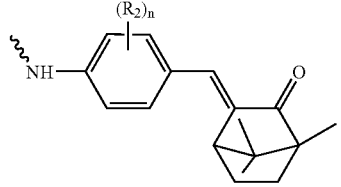
(7)

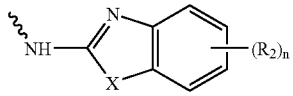
(8)

in which:

$R_2$ is a linear or branched $C_1$-$C_8$ alkyl radical n is 0, 1 or 2; the radicals A, which may be identical or different, are each an alkali metal cation, an ammonium group, a $C_1$-$C_{20}$ mono-, di- or trialkylammonium radical, a $C_2$-$C_{20}$ mono-, di- or trialkanolammonium radical, or a $C_5$-$C_8$ quaternary nitrogen-containing heterocyclic ring member; $R_3$ is a linear or branched $C_1$-$C_{20}$ alkyl radical, or a linear or branched $C_2$-$C_{20}$ alkenyl radical, said radicals optionally containing one or more oxygen atoms, silicon atoms or trisiloxane groups; $R_4$ is a linear or branched $C_1$-$C_{20}$ alkyl radical, a linear or branched $C_2$-$C_{20}$ alkenyl radical, or a linear or branched $C_1$-$C_{20}$ alkoxy radical, said radicals optionally containing one or more oxygen atoms, silicon atoms or trisiloxane groups; $R_5$ is hydrogen or OH, and X is O, S or $NR_6$, wherein $R_6$ is H or a linear or branched $C_1$-$C_4$ alkyl radical; or (ii) an OH; a linear or branched $C_1$-$C_{20}$ alkoxy radical, or a linear or branched $C_1$-$C_{20}$ mono- or dialkylamino radical, said radicals optionally containing one or more oxygen atoms, silicon atoms or trisiloxane groups.

2. A water-soluble substituted s-triazine compound as defined by claim 1, where in formula (1), said other radical which may be identical or different, is either:

(i) a chromophore of one of the formulae:

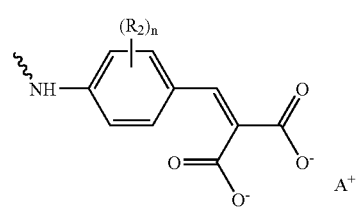
(2)

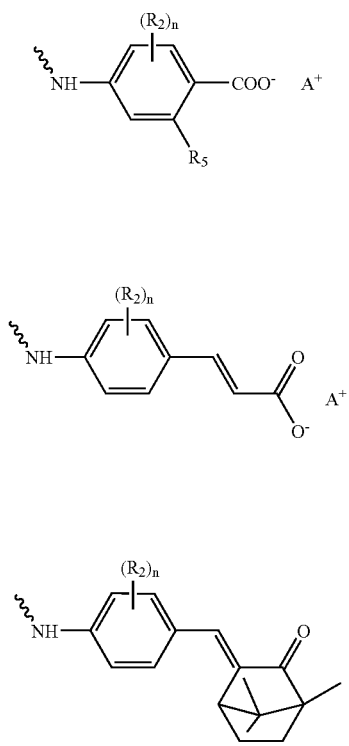

in which A is Na, K or triethanolamine n= 0; and $R_5$ is hydrogen or OH; or (ii) an OH radical, a $C_1$-$C_4$ alkoxy radical, or a $C_1$-$C_4$ dialkylamino radical.

3. A water-soluble substituted s-triazine compound as defined by claim 1, having the formula selected from the group consisting of:

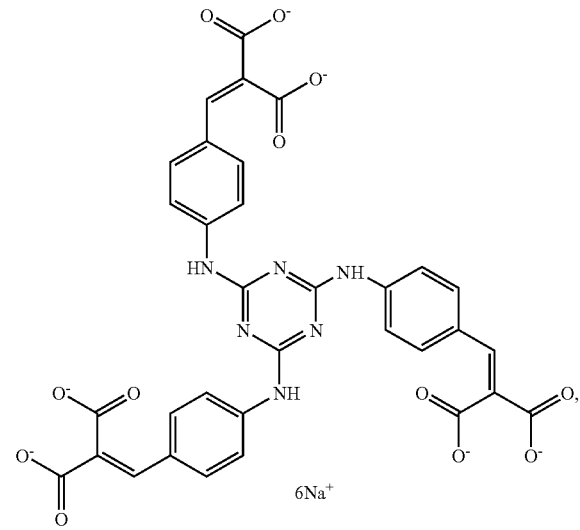

(compound a).

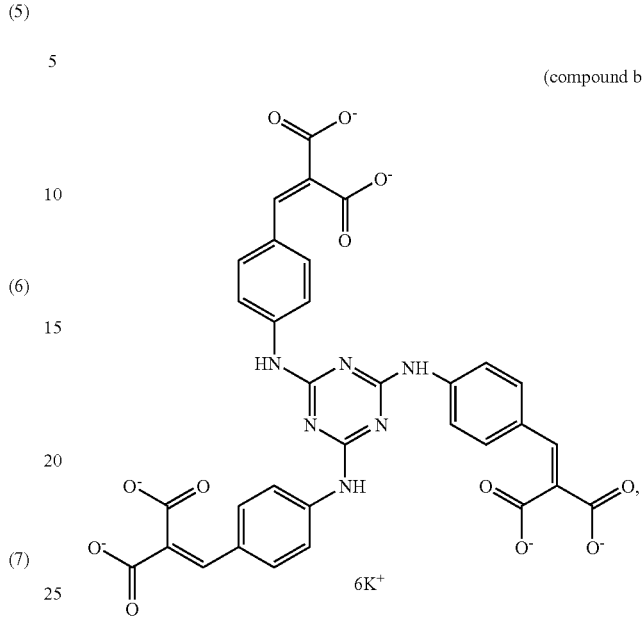

(compound b).

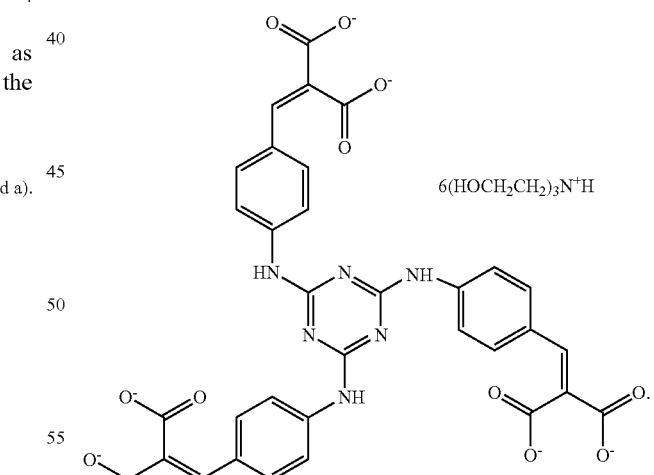

(compound c).

4. A water-soluble substituted s-triazine compound as defined by claim 1, having the formula selected from the group consisting of:

(compound d).
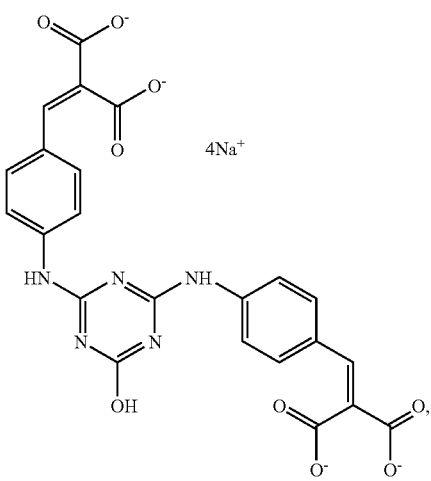
(compound e).
(compound f).
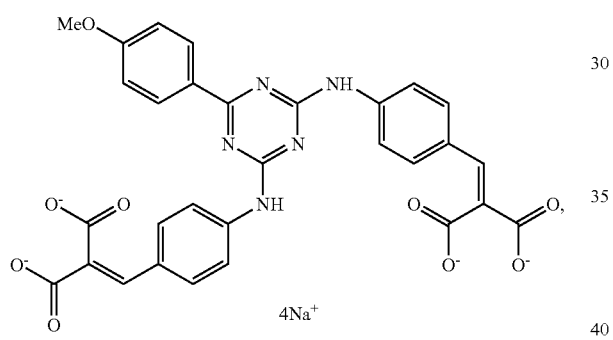
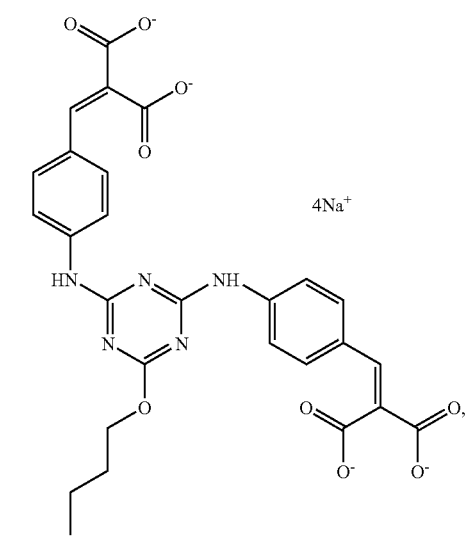
-continued
(compound h).
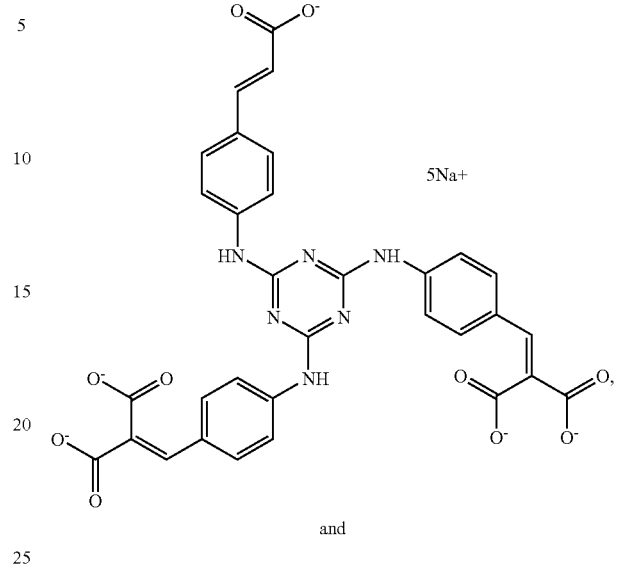
and
(compound i).
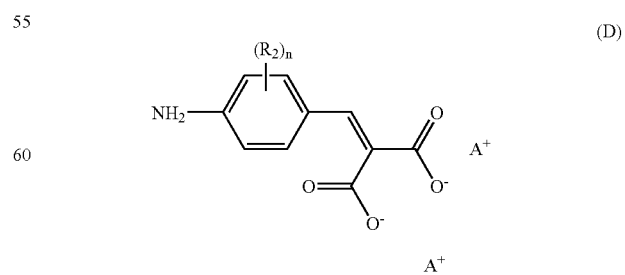
5. A process for the preparation of a water-soluble substituted s-triazine compound as defined by claim 1, comprising reacting an aminobenzalmalonate of formula (D)
(D)
with (i) a compound of formula (B):

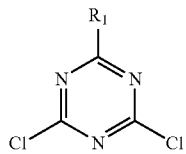
(B)

when the compound of formula (1) contains two substituents of formula (2), or (ii) with a compound of formula (A):

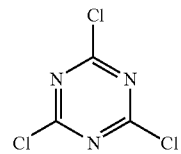
(A)

when the compound of formula (1) contains three substituents of formula (2).

6. The process as defined by claim 5, carried out in homogeneous aqueous medium or in suspension, the pH being adjusted during the reaction to a value not exceeding 9.5 and at a temperature of between +5° C.-120°C.

7. The process as defined by claim 6, carried out in the presence of an acetone, THF or toluene organic cosolvent.

8. The process as defined by claim 6, carried out in the presence of sodium hydroxide, potassium hydroxide, sodium carbonate or sodium bicarbonate.

9. A topically applicable cosmetic/dermatological sunscreen composition suited for the UV-photoprotection of human skin/keratinous materials, comprising an effective UV-photoprotecting amount of at least one water-soluble substituted s-triazine compound as claimed in claim 1, formulated into a topically applicable, cosmetically/dermatologically acceptable medium therefor.

10. The cosmetic/dermatological sunscreen composition as defined by claim 9, where in formula (1), said other radical which may be identical or different, is either:

(i) a chromophore of one of the formulae:

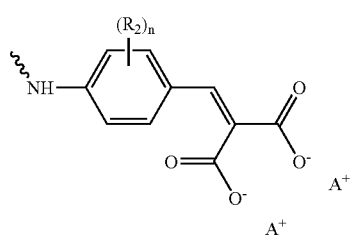
(2)

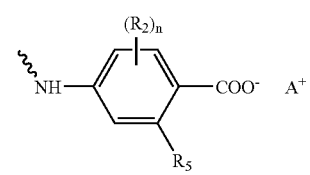
(5)

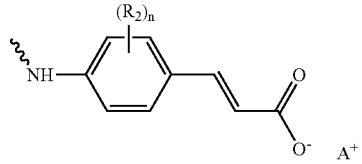
(6)

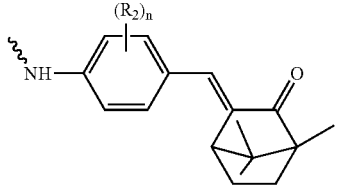
(7)

in which A is Na, K or triethanolamine n= 0; and $R_5$ is hydrogen or OH;

(ii) or an OH radical, a $C_1$-$C_4$ alkoxy radical, or a $C_1$-$C_4$ dialkylamino radical.

11. The cosmetic/dermatological sunscreen composition as defined by claim 9, said at least one water-soluble substituted s-triazine compound of formula (1) comprising from 0.01% to 20% by weight thereof.

12. The cosmetic/dermatological sunscreen composition as defined by claim 9, said at least one water-soluble substituted s-triazine compound of formula (1) comprising from 0.1% to 10% by weight thereof.

13. The cosmetic/dermatological sunscreen composition as defined by claim 9, comprising an oil-in-water or water-in-oil emulsion.

14. The cosmetic/dermatological sunscreen composition as defined by claim 9, further comprising one or more complementary organic or inorganic sunscreens which are active in UV-A and/or UV-B regions.

15. The cosmetic/dermatological sunscreen composition as defined by claim 14, comprising one or more complementary organic sunscreens selected from the group consisting of menthyl anthranilate; cinnamic derivatives selected from the group consisting of ethylhexyl methoxycinnamate, isopropyl methoxycinnamate, isoamyl methoxycinnamate, cinoxate, DEA methoxycinnamate, diisopropyl methylcinnamate, glyceryl ethylhexanoate and dimethoxycinnamate; dibenzoylmethane derivatives selected from the group consisting of butyl methoxyd ibenzoylmethaneand isopropyl d ibenzoylmethane;salicylic derivatives selected from the group consisting of homosalate, ethylhexyl salicylate, dipropylene glycol salicylate, and TEA salicylate; camphor derivatives selected from the group consisting of 3-benzylidene camphor, 4-methylbenzylidene camphor, benzylidene camphor sulphonic acid, camphor benzalkonium methosulphate, terephthalylidene dicamphor sulphonic Acid, and polyacrylamidomethyl benzylidene camphor; triazine derivatives selected from the group consisting of anisotriazine, ethylhexyl triazone, 2,4,6-tris(diisobutyl 4'-aminobenzalmalonate)-s-triazine, and diethylhexyl butamido triazone; benzophenone derivatives selected from the group consisting of benzophenone-1, benzophenone-2, benzophenone-3, benzophenone-4, benzophenone-5, Benzophenone-6, benzophenone-8, benzophenone-9, benzophenone-12, and n-hexyl 2-(4-diethylamino-2-hydroxybenzoyl)benzoate; β,β-diphenylacrylate derivatives selected from the group consisting of octocrylene and etocrylene; benzotriazole derivatives selected from the group consisting of drometrizole trisiloxane and methylene bis-benzotriazolyl tetramethylbutyiphenol; polysilicone-15; benzimidazole derivatives selected from the group consisting of phenylbenzimidazole suiphonic acid, and disodium phenyl dibenzimidazole ttra-suiphonate; ethyihexyl dimethoxybenzylidene dioxoimidazoline propionate; p-aminobenzoic acid (PABA) derivatives selected from the group consisting of PABA, Ethyl PABA, Ethyl Dihydroxypropyl PABA, Ethylhexyl Dimethyl PABA, Glyceryl PABA and PEG-25 PABA; 2,4-bis[5-(d imethylpropyl)benzoxazol-2-yl(4- phenyl)imino]-6-(2-ethylhexyl)imino-1,3,5-triazine; polymer sunscreens and silicone sunscreens; dimers derived from α-alkylstyrene; 4,4-diarylbutadienes and mixtures thereof.

16. The cosmetic/dermatological sunscreen composition as defined by claim 15, said one or more complementary organic sunscreens being selected from the group consisting of:
   Ethylhexyl Salicylate,
   Ethylhexyl Methoxycinnamate,
   Butyl Methoxydibenzoylmethane,
   Octocrylene,
   Phenylbenzimidazole Sulphonic Acid,
   Benzophenone-3,
   Benzophenone-4,
   Benzophenone-5,
   n-Hexyl 2-(4-diethylamino-2-hydroxybenzoyl)benzoate,
   4-Methylbenzylidene camphor,
   Terephthalylidene Dicamphor Sulphonic Acid,
   Disodium Phenyl Dibenzimidazole Tetra-sulphonate,
   2,4,6-tris(Diisobutyl 4'-aminobenzalmalonate)-s-triazine,
   Anisotriazine,
   Ethylhexyl triazone,
   Diethylhexyl Butamido Triazone,
   Methylene bis-Benzotriazolyl Tetramethylbutylphenol,
   Drometrizole Trisiloxane,
   Polysilicone-15,
   1,1-Dicarboxy(2,2N-dimethylpropyl)-4,4-diphenylbutadiene,
   2,4-bis[5-(Dimethylpropyl)benzoxazol-2-yl- (4-Phenyl)imino]-6-(2-ethylhexyl)imino-1,3,5-triazine, and mixtures thereof.

17. The cosmetic/dermatological sunscreen composition as defined by claim 14, comprising one or more complementary inorganic sunscreens which comprise coated or uncoated metal oxide pigments or nanopigments.

18. The cosmetic/dermatological sunscreen composition as defined by claim 17, said one or more pigments or nanopigments comprising coated or uncoated titanium oxide, zinc oxide, iron oxide, zirconium oxide, cerium oxide or mixtures thereof.

19. The cosmetic/dermatological sunscreen composition as defined by claim 9, further comprising at least one tanning and/or artificial skin browning agent.

20. The cosmetic/dermatological sunscreen composition as defined by claim 9, further comprising at least one adjuvant selected from the group consisting of fats, organic solvents, ionic and nonionic thickeners, softeners, humectants, antioxidants, moisturizers, desquamating agents, free-radical scavengers, antipollutants, antibacterials, anti-inflammatories, depigmenting agents, propigmenting agents, opacifiers, stabilizers, emollients, silicones, antifoams, insect repellants, perfumes, preservatives, anionic, cationic, nonionic, zwitterionic and amphoteric surfactants, substance P antagonists, substance CGRP antagonists, fillers, pigments, colorants, polymers, propellants, alkalifying, and acidifying agents.

21. The cosmetic/dermatological sunscreen composition as defined by claim 9, comprising a nonionic vesicle dispersion, a lotion, a paste, a cream, a milk, a gel, a cream gel, a suspension, an ointment, a dispersion, an oil, a powder, a solid stick, a foam or a spray.

22. The cosmetic/dermatological sunscreen composition as defined by claim 9, comprising a shampoo, hair lotion, hair gel, hair emulsion, nonionic vesicle dispersion, or a makeup for the eyelashes, eyebrows, nails or skin.

23. A regime or regimen for photoprotecting human skin/keratinous Materials against the damaging effects of UV-radiation, comprising topically applying thereon a thus effective amount of the cosmetic/dermatological sunscreen composition as defined by claim 9.

24. A regime or regimen for controlling the change in the color of human skin brought about by exposure to UV-radiation, comprising topically applying thereon a thus effective amount of the cosmetic/dermatological sunscreen composition as defined by claim 9.

* * * * *